(12) United States Patent
Salahieh et al.

(10) Patent No.: US 12,370,358 B2
(45) Date of Patent: *Jul. 29, 2025

(54) INTRAVASCULAR BLOOD PUMPS AND METHODS OF USE AND MANUFACTURE

(71) Applicant: Shifamed Holdings, LLC, Campbell, CA (US)

(72) Inventors: Amr Salahieh, Saratoga, CA (US); Tom Saul, Portland, OR (US); Brady Esch, San Jose, CA (US); Anna Kerlo, Milpitas, CA (US); Daniel Hildebrand, Santa Cruz, CA (US); Daniel Varghai, Scotts Valley, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/615,896

(22) Filed: Mar. 25, 2024

(65) Prior Publication Data
US 2025/0050091 A1 Feb. 13, 2025

Related U.S. Application Data

(63) Continuation of application No. 17/552,311, filed on Dec. 15, 2021, now Pat. No. 12,076,545, which is a
(Continued)

(51) Int. Cl.
*A61M 60/148* (2021.01)
*A61M 60/139* (2021.01)
(Continued)

(52) U.S. Cl.
CPC ........ *A61M 60/148* (2021.01); *A61M 60/139* (2021.01); *A61M 60/174* (2021.01); *A61M 60/237* (2021.01); *A61M 60/414* (2021.01); *A61M 60/804* (2021.01); *A61M 60/818* (2021.01)

(58) Field of Classification Search
CPC .............. A61M 60/148; A61M 60/139; A61M 60/174; A61M 60/237; A61M 60/414; A61M 60/804; A61M 60/818; A61M 60/81; A61M 2207/10; A61M 60/808; A61M 60/857; A61M 60/865; A61M 60/13
See application file for complete search history.

(56) References Cited

U.S. PATENT DOCUMENTS 4,625,712 A 12/1986 Wampler
4,753,221 A 6/1988 Kensey et al.
(Continued)

FOREIGN PATENT DOCUMENTS

CA 3014105 A1 8/2017
EP 3131599 A1 2/2017
(Continued)

*Primary Examiner* — Mark W. Bockelman
(74) *Attorney, Agent, or Firm* — Shay Glenn LLP

(57) ABSTRACT

Devices for moving blood within a patient, and methods of doing so. The devices can include a pump portion that includes an impeller and a housing around the impeller, as well as a fluid lumen. The impeller can be activated to cause rotation of the impeller and thereby move fluid within the fluid lumen.

20 Claims, 9 Drawing Sheets

Related U.S. Application Data continuation of application No. 16/714,382, filed on Dec. 13, 2019, now Pat. No. 11,229,784, which is a continuation of application No. 16/265,828, filed on Feb. 1, 2019, now Pat. No. 10,722,631.

(60) Provisional application No. 62/625,312, filed on Feb. 1, 2018.

(51) Int. Cl.
*A61M 60/174* (2021.01)
*A61M 60/237* (2021.01)
*A61M 60/414* (2021.01)
*A61M 60/804* (2021.01)
*A61M 60/818* (2021.01)

(56) References Cited

U.S. PATENT DOCUMENTS

| | | | |
|---|---|---|---|
| 4,846,152 A | 7/1989 | Wampler et al. | |
| 5,061,256 A | 10/1991 | Wampler | |
| 5,287,858 A | 2/1994 | Hammerslag et al. | |
| 5,507,629 A | 4/1996 | Jarvik | |
| 5,735,892 A | 4/1998 | Myers et al. | |
| 6,007,478 A | 12/1999 | Siess et al. | |
| 6,053,943 A | 4/2000 | Edwin et al. | |
| 6,685,696 B2 | 2/2004 | Fleischhacker et al. | |
| 6,712,844 B2 | 3/2004 | Pacetti | |
| 7,022,100 B1 | 4/2006 | Aboul Hosn et al. | |
| 7,027,875 B2 | 4/2006 | Siess et al. | |
| 7,220,275 B2 | 5/2007 | Davidson et al. | |
| 7,828,710 B2 | 11/2010 | Shifflette | |
| 8,388,565 B2 | 3/2013 | Shifflette | |
| 8,485,961 B2 | 7/2013 | Campbell et al. | |
| 8,535,211 B2 | 9/2013 | Campbell et al. | |
| 8,591,393 B2 | 11/2013 | Walters et al. | |
| 8,597,170 B2 | 12/2013 | Walters et al. | |
| 8,721,517 B2 | 5/2014 | Zeng et al. | |
| 8,734,508 B2 | 5/2014 | Hastings et al. | |
| 8,814,776 B2 | 8/2014 | Hastie et al. | |
| 8,814,933 B2 | 8/2014 | Siess | |
| 8,849,398 B2 | 9/2014 | Evans | |
| 8,932,141 B2 | 1/2015 | Liebing | |
| 8,934,956 B2 | 1/2015 | Glenn et al. | |
| 9,028,216 B2 | 5/2015 | Schumacher et al. | |
| 9,028,392 B2 | 5/2015 | Shifflette | |
| 9,072,825 B2 | 7/2015 | Pfeffer et al. | |
| 9,138,518 B2 | 9/2015 | Campbell et al. | |
| 9,180,235 B2 | 11/2015 | Forsell | |
| 9,446,179 B2 | 9/2016 | Keenan et al. | |
| 9,512,839 B2 | 12/2016 | Liebing | |
| 9,833,550 B2 | 12/2017 | Siess | |
| 9,872,948 B2 | 1/2018 | Siess | |
| 10,052,419 B2 | 8/2018 | Er | |
| 10,208,763 B2 | 2/2019 | Schumacher et al. | |
| 10,357,598 B2 | 7/2019 | Aboul-Hosn et al. | |
| 10,722,631 B2 * | 7/2020 | Salahieh | A61M 60/148 |
| 10,881,770 B2 | 1/2021 | Tuval et al. | |
| 10,894,115 B2 | 1/2021 | Pfeffer et al. | |
| 11,229,784 B2 * | 1/2022 | Salahieh | A61M 60/857 |
| 11,268,521 B2 | 3/2022 | Toellner | |
| 11,280,345 B2 | 3/2022 | Bredenbreuker et al. | |
| 11,511,103 B2 | 11/2022 | Salahieh et al. | |
| 11,850,413 B2 | 12/2023 | Zeng et al. | |
| 12,017,056 B2 | 6/2024 | Guo et al. | |
| 12,076,545 B2 * | 9/2024 | Salahieh | A61M 60/808 |
| 2005/0277803 A1 | 12/2005 | Pecor | |
| 2007/0250148 A1 | 10/2007 | Perry et al. | |
| 2007/0265673 A1 | 11/2007 | Ransbury et al. | |
| 2014/0148638 A1 | 5/2014 | LaRose et al. | |
| 2015/0238671 A1 | 8/2015 | Mesallum | |
| 2015/0328382 A1 | 11/2015 | Corbett et al. | |
| 2016/0022890 A1 | 1/2016 | Schwammenthal et al. | |
| 2016/0053763 A1 | 2/2016 | Toellner | |
| 2017/0014562 A1 | 1/2017 | Liebing | |
| 2017/0037860 A1 | 2/2017 | Toellner | |
| 2017/0100527 A1 | 4/2017 | Schwammenthal et al. | |
| 2017/0173242 A1 | 6/2017 | Anderson et al. | |
| 2017/0232169 A1 | 8/2017 | Muller | |
| 2017/0340788 A1 | 11/2017 | Korakianitis et al. | |
| 2018/0080326 A1 | 3/2018 | Schumacher et al. | |
| 2018/0149164 A1 | 5/2018 | Siess | |
| 2018/0303990 A1 | 10/2018 | Siess et al. | |
| 2020/0121835 A1 | 4/2020 | Farago et al. | |
| 2020/0237981 A1 | 7/2020 | Tuval et al. | |
| 2020/0316268 A1 | 10/2020 | Antoni et al. | |
| 2021/0052794 A1 | 2/2021 | Tuval et al. | |
| 2022/0203084 A1 | 6/2022 | Zarins et al. | |
| 2023/0310830 A1 | 10/2023 | Salahieh et al. | |
| 2024/0139499 A1 | 5/2024 | Salahieh et al. | |

FOREIGN PATENT DOCUMENTS

| | | |
|---|---|---|
| EP | 3153190 A1 | 4/2017 |
| EP | 3000493 B1 | 5/2017 |
| WO | WO01/019444 A1 | 3/2001 |
| WO | WO2015/177793 A2 | 11/2015 |
| WO | WO2018/061002 A1 | 4/2018 |
| WO | WO2018/067410 A1 | 4/2018 |
| WO | WO2018/078615 A1 | 5/2018 |
| WO | WO2018/088939 A1 | 5/2018 |
| WO | WO2018/096531 A1 | 5/2018 |
| WO | WO2019/191851 A1 | 9/2019 |
| WO | WO2019/194956 A1 | 10/2019 |

* cited by examiner

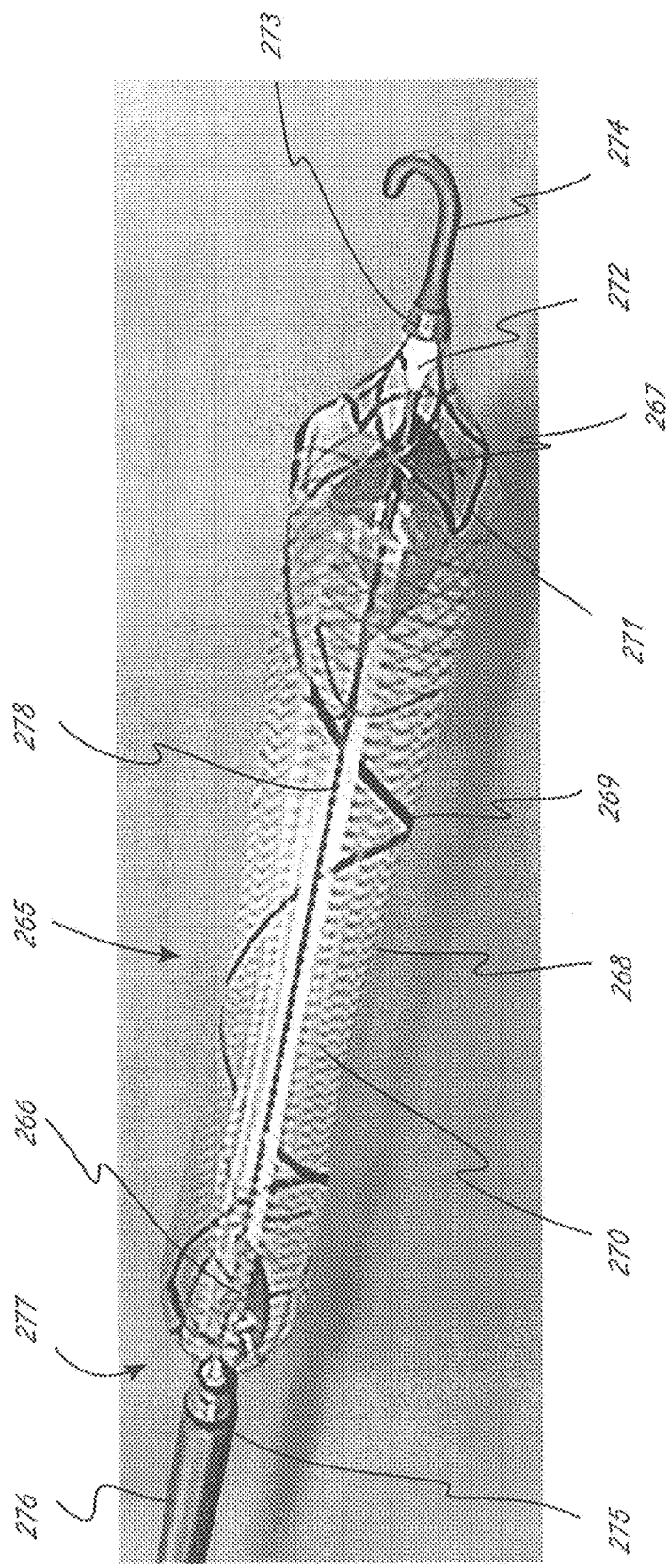

INTRAVASCULAR BLOOD PUMPS AND METHODS OF USE AND MANUFACTURE

CROSS REFERENCE TO RELATED APPLICATIONS

This application is a continuation of U.S. application Ser. No. 17/552,311, filed Dec. 15, 2021, which is a continuation of U.S. application Ser. No. 16/714,382, filed Dec. 13, 2019, now U.S. Pat. No. 11,229,784, which is a continuation of U.S. application Ser. No. 16/265,828, filed Feb. 1, 2019, now U.S. Pat. No. 10,722,631, which claims priority to the following U.S. Provisional Patent Application, the disclosures of which are fully incorporated by reference herein for all purposes: Application No. 62/625,312, filed Feb. 1, 2018.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

This disclosure relates generally to intravascular fluid movement devices such as blood pump, and their methods of use and manufacture.

One aspect of the disclosure is an intravascular blood pump, comprising: a collapsible housing comprising a fluid lumen, the fluid lumen having a distal end, a proximal end, and a substantially constant diameter portion having a proximal end, wherein the fluid lumen proximal end is proximal to the proximal end of the substantially constant diameter portion; a collapsible distal impeller axially spaced from a collapsible proximal impeller, the distal impeller having an expanded configuration and the proximal impeller having an expanded configuration, wherein the proximal impeller has an axial length in the expanded configuration, and at least a portion of the proximal impeller is disposed in the substantially constant diameter portion and at least a portion of the of the proximal impeller, measured along the axial length, is disposed proximal to the proximal end of the substantially constant diameter portion.

In some embodiments, at least 20% and up to 90% of the proximal impeller (axial length) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, optionally up to 35% of the impeller, optionally up to 30% of the impeller, optionally up to 25% of the impeller, is disposed proximal to a proximal end of the constant diameter portion.

In some embodiments, at least 25% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 30% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 35% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 40% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller is disposed proximal to a proximal end of the constant diameter portion.

In some embodiments, at least 45% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller is disposed proximal to a proximal end of the constant diameter portion.

In some embodiments, at least 50% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller is disposed proximal to a proximal end of the constant diameter portion.

In some embodiments, at least 55% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller is disposed proximal to a proximal end of the constant diameter portion.

In some embodiments, at least 60% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller is disposed proximal to a proximal end of the constant diameter portion.

In some embodiments, at least 65% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller is disposed proximal to a proximal end of the constant diameter portion.

In some embodiments, at least 70% and up to 90% of the proximal impeller (measured axially) is disposed proximal to a proximal end of the constant diameter portion, optionally up to 85% of the impeller, optionally up to 80% of the impeller, optionally up to 75% of the impeller, is disposed proximal to a proximal end of the constant diameter portion.

In some embodiments, at least 75% and up to 90% of the proximal impeller (measured axially) is disposed proximal to a proximal end of the constant diameter portion, optionally up to 85% of the impeller, optionally up to 80% of the impeller is disposed proximal to a proximal end of the constant diameter portion.

In some embodiments, at least 80% and up to 90% of the proximal impeller (measured axially) is disposed proximal to a proximal end of the constant diameter portion, optionally up to 85% of the impeller is disposed proximal to a proximal end of the constant diameter portion.

A portion of the proximal impeller can extend further proximally that the fluid lumen proximal end when the proximal impeller is in the expanded configuration.

The fluid lumen can further comprise a proximal portion disposed proximal to the substantially constant diameter portion, the proximal portion including at least one surface adapted and configured to behave as a fluid diffuser. The proximal portion can comprise a flared configuration. The proximal portion can have a continuous and gradual flare from the proximal end of the substantially constant diameter portion to the fluid lumen proximal end. The proximal portion can have any other proximal portion configuration disclosed herein.

The collapsible housing can comprise a collapsible support structure coupled to a collapsible membrane.

One aspect of the disclosure is an intravascular blood pump, comprising: a collapsible housing comprising a fluid lumen, the fluid lumen having a distal end and a flared proximal region that has a distal end that is proximal to the fluid lumen distal end, the flared proximal region comprising at least one surface adapted and configured to behave as a fluid diffuser, a collapsible distal impeller axially spaced from a collapsible proximal impeller, the distal impeller having an expanded configuration and the proximal impeller having an expanded configuration, at least a portion of the proximal impeller disposed distal to the distal end of the flared proximal region, wherein the proximal impeller has an axial length in the expanded configuration, and at least a portion of the proximal impeller, measured along the axial length, is disposed proximal to the distal end of the flared proximal region.

In some embodiments, at least 20% and up to 90% of the proximal impeller (axial length) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, optionally up to 35% of the impeller, optionally up to 30% of the impeller, optionally up to 25% of the impeller, is disposed proximal to the distal end of the flared proximal region.

In some embodiments, at least 25% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to the distal end of the flared proximal region.

In some embodiments, at least 30% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to the distal end of the flared proximal region.

In some embodiments, at least 35% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to the distal end of the flared proximal region.

In some embodiments, at least 40% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller is disposed proximal to the distal end of the flared proximal region.

In some embodiments, at least 45% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller is disposed proximal to the distal end of the flared proximal region.

In some embodiments, at least 50% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller is disposed proximal to the distal end of the flared proximal region.

In some embodiments, at least 55% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller is disposed proximal to the distal end of the flared proximal region.

In some embodiments, at least 60% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller is disposed proximal to the distal end of the flared proximal region.

In some embodiments, at least 65% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller is disposed proximal to the distal end of the flared proximal region.

In some embodiments, at least 70% and up to 90% of the proximal impeller (measured axially) is disposed proximal to the distal end of the flared proximal region, optionally up to 85% of the impeller, optionally up to 80% of the impeller, optionally up to 75% of the impeller, is disposed proximal to the distal end of the flared proximal region.

In some embodiments, at least 75% and up to 90% of the proximal impeller (measured axially) is disposed proximal to the distal end of the flared proximal region, optionally up to 85% of the impeller, optionally up to 80% of the impeller is disposed proximal to the distal end of the flared proximal region.

In some embodiments, at least 80% and up to 90% of the proximal impeller (measured axially) is disposed proximal to the distal end of the flared proximal region, optionally up to 85% of the impeller is disposed proximal to the distal end of the flared proximal region.

A portion of the proximal impeller can extend further proximally that the fluid lumen proximal end when the proximal impeller is in the expanded configuration.

The fluid lumen can further comprise a substantially constant diameter portion distal to the flared proximal region.

The flared proximal region can have a continuous and gradual flare from the distal end of the flared region to the fluid lumen proximal end.

One aspect of the disclosure is an intravascular blood pump, comprising: a collapsible housing comprising a fluid lumen, the fluid lumen having a distal end, a proximal end, and a substantially constant diameter portion having a proximal end; a collapsible distal impeller axially spaced from a collapsible proximal impeller, the distal impeller having an expanded configuration and the proximal impeller having an expanded configuration, at least a portion of the proximal impeller is disposed in the substantially constant diameter portion, wherein the proximal impeller has an axial length in the expanded configuration, and a midpoint halfway along the axial length, wherein the midpoint is proximal to the proximal end of the substantially constant diameter portion.

One aspect of the disclosure is an intravascular blood pump, comprising: a collapsible housing comprising a fluid lumen, the fluid lumen having a distal end and a proximal end; a collapsible distal impeller axially spaced from a collapsible proximal impeller, the distal impeller having an expanded configuration and the proximal impeller having an expanded configuration, and at least a portion of each of the distal and proximal impellers disposed between the distal and proximal ends of the fluid lumen, wherein the proximal impeller and the distal impeller are each, when in their expanded configurations and when rotated, positioned relative to the fluid lumen such that the proximal impeller is performing more than 50% of the work of the blood pump and the distal impeller is performing less than 50% of the work of the blood pump.

The blood pump can include any other blood pump feature included herein, such as the relative axial positions of the proximal impeller relative to the fluid lumen.

The blood pump may not include a vane disposed axially between the proximal and distal impellers.

The blood pump may not include a stator blade disposed axially between the proximal and distal impellers.

At least half of the proximal impeller, measured along an axial length, can be disposed proximal to a proximal end of a substantially constant diameter portion of the fluid lumen.

At least half of the proximal impeller, measured along an axial length, can be disposed in a flared proximal region of the fluid lumen.

A proximal impeller and a distal impeller can each, when in their expanded configurations, be positioned relative to the fluid lumen such that the proximal impeller is performing more than 55% of the work of the blood pump and the distal impeller is performing less than 45% of the work of the blood pump.

A proximal impeller and a distal impeller can each, when in their expanded configurations, be positioned relative to the fluid lumen such that the proximal impeller is performing more than 60% of the work of the blood pump and the distal impeller is performing less than 40% of the work of the blood pump.

A proximal impeller and a distal impeller can each, when in their expanded configurations, be positioned relative to the fluid lumen such that the proximal impeller is performing more than 70% of the work of the blood pump and the distal impeller is performing less than 30% of the work of the blood pump.

A proximal impeller and a distal impeller can each, when in their expanded configurations, be positioned relative to the fluid lumen such that the proximal impeller is performing more than 80% of the work of the blood pump and the distal impeller is performing less than 20% of the work of the blood pump.

One aspect of the disclosure is method of intravascularly pumping blood in a subject, comprising: positioning a pump housing fluid lumen first end in a first anatomical location (e.g., a left ventricle); positioning a distal impeller of the blood pump in the first anatomical location; positioning a proximal impeller of the blood pump in a second anatomical location (e.g., an ascending aorta); positioning a pump housing fluid lumen second end in the second anatomical location; positioning at least a portion of a central region of the fluid lumen across tissue (e.g., an aortic valve), creating a flow path between the fluid lumen first end positioned in the first anatomical region and the fluid lumen second end positioned in the second anatomical location such that the distal impeller and the proximal impeller can pump blood through the fluid lumen.

The method can include rotating the distal impeller and proximal impeller and thereby causing the proximal impeller to perform more than 50% of the work of the blood pump and the distal impeller to perform less than 50% of the work of the blood pump.

The rotating step can comprise rotating the distal impeller and proximal impeller and thereby causing the proximal impeller to perform more than 60% of the work of the blood pump and the distal impeller to perform less than 40% of the work of the blood pump.

The rotating step can comprise rotating the distal impeller and proximal impeller and thereby causing the proximal impeller to perform more than 70% of the work of the blood pump and the distal impeller to perform less than 30% of the work of the blood pump.

The rotating step can comprise rotating the distal impeller and proximal impeller and thereby causing the proximal impeller to perform more than 75% of the work of the blood pump and the distal impeller to perform less than 25% of the work of the blood pump.

The rotating step can comprise rotating the distal impeller and proximal impeller and thereby causing the proximal impeller to perform about 80% of the work of the blood pump and the distal impeller to perform about 20% of the work of the blood pump.

One aspect of the disclosure is an intravascular blood pump, comprising: a collapsible housing comprising a fluid lumen, the fluid lumen having a distal end and a proximal end; a collapsible distal impeller axially spaced from a collapsible proximal impeller, the distal impeller having an expanded configuration and the proximal impeller having an expanded configuration, and at least a portion of each of the distal and proximal impellers disposed between the distal and proximal ends of the fluid lumen, wherein the proximal impeller and the distal impeller are each, when in their expanded configurations and when rotated, positioned relative to the fluid lumen such that the proximal impeller is generating more than 50% of the pressure generated by the blood pump and the distal impeller is generating less than 50% of the pressure generated by the blood pump of the blood pump.

The blood pump may not include a vane disposed axially between the proximal and distal impellers.

The blood pump may not include a stator blade disposed axially between the proximal and distal impellers.

The proximal impeller and the distal impeller can each be, when in their expanded configurations, positioned relative to the fluid lumen such that the proximal impeller is generating more than 55% of the pressure generated by the blood pump and the distal impeller is generating less than 45% of the pressure generated by the blood pump.

The proximal impeller and the distal impeller can are each be, when in their expanded configurations, positioned relative to the fluid lumen such that the proximal impeller is generating more than 60% of the pressure generated by the blood pump and the distal impeller is generating less than 40% of the pressure generated by the blood pump.

The proximal impeller and the distal impeller can each be, when in their expanded configurations, positioned relative to the fluid lumen such that the proximal impeller is generating more than 70% of the pressure generated by the blood pump and the distal impeller is generating less than 30% of the pressure generated by the blood pump.

The proximal impeller and the distal impeller can each be, when in their expanded configurations, positioned relative to the fluid lumen such that the proximal impeller is generating about 80% of the pressure generated by the blood pump and the distal impeller is generating about 20% of the pressure generated by the blood pump.

One aspect of the disclosure is an intravascular blood pump, comprising: a collapsible housing comprising a fluid lumen, the fluid lumen having a distal end, a proximal end, and a substantially constant diameter portion having a proximal end, wherein the fluid lumen proximal end is proximal to the proximal end of the substantially constant diameter portion; a collapsible distal impeller axially spaced from a collapsible proximal impeller, the distal impeller having an expanded configuration and the proximal impeller having an expanded configuration, at least a portion of the proximal impeller is disposed in the substantially constant diameter portion, wherein the proximal impeller has an axial length in the expanded configuration.

Any other features of a blood pump herein can be incorporated into this aspect.

One aspect of the disclosure is an intravascular blood pump, comprising: a collapsible housing comprising a fluid lumen, the fluid lumen having a distal end, a proximal end, and a proximal region with a lumen wall configuration, the proximal region including the proximal end; a collapsible distal impeller axially spaced from a collapsible proximal impeller, the distal impeller having an expanded configuration and the proximal impeller having an expanded, at least a portion of the proximal impeller disposed distal to the proximal region of the fluid lumen; wherein the proximal impeller has at least one blade with a surface, the at least one blade surface and the lumen wall configured such that if the proximal impeller is moved at least 2 mm proximally relative to an initial position such that less of the proximal impeller is disposed distal to the proximal region of fluid lumen, the change in axial position of the proximal impeller results in at least a 10% in flow.

This disclosure includes methods of manufacturing any and all of the blood pumps herein.

This disclosure includes methods of using any and all of the blood pumps herein, examples of which are provided herein in some exemplary anatomical locations.

Any of the axial spacing between proximal and distal impellers described herein can be applied to any of the embodiments herein, including any embodiments in the Claims, Description, or Summary sections.

BRIEF DESCRIPTION OF THE DRAWINGS

FIG. 5 illustrates an exemplary working portion.

DETAILED DESCRIPTION

The present disclosure is related to medical devices, systems, and methods of use and manufacture. Medical devices herein may include a distal working portion adapted to be disposed within a physiologic vessel, wherein the distal working portion includes one or more components that act upon fluid. For example, distal working portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein unless specifically indicated otherwise.

Figure 1:
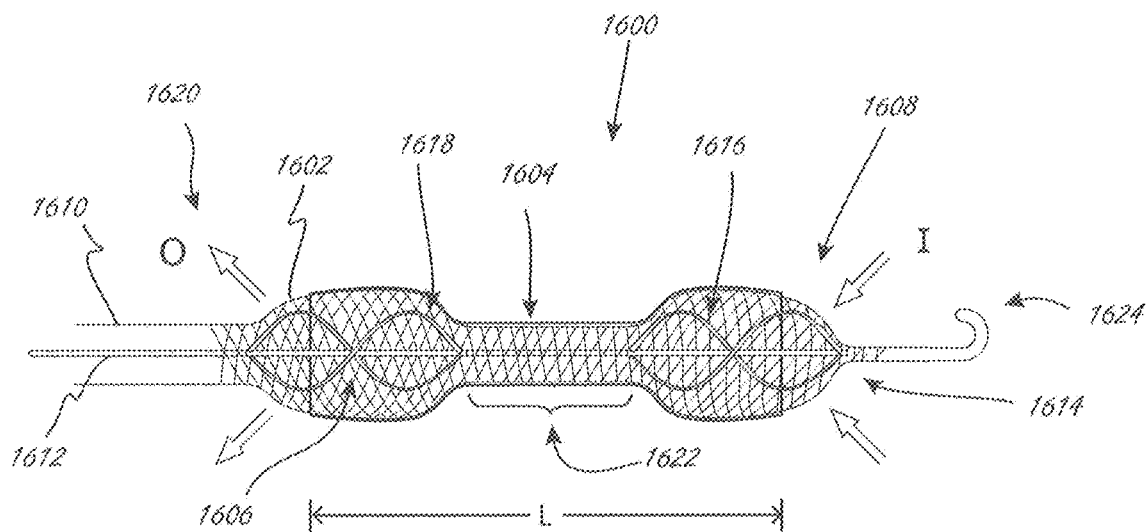
FIG. 1 is a side view of an exemplary working portion that includes a conduit, a plurality of impellers, an expandable member.

FIG. 1 is a side view illustrating a distal portion of an exemplary intravascular fluid pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can be attached to drive cable 1612. Drive cable 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Pump portion 1600 also includes expandable member 1602, which in this embodiment has a proximal end 1620 that extends further proximally than a proximal end of proximal impeller 1606, and a distal end 1608 that extends further distally than a distal end 1614 of distal impeller 1616. Expandable member 1602 is disposed radially outside of the impellers along the axial length of the impellers. Expandable member 1602 can be constructed in a manner and made from materials similar to many types of expandable structures that are known in the medical arts to be able to collapsed and expanded, examples of which are provided herein. Examples of suitable materials include, but are not limited to, polyurethane and polyurethane elastomers.

Pump portion 1600 also includes conduit 1604, which is coupled to expandable member 1602, has a length L, and extends axially between the impellers. Conduit 1604 creates and provides a fluid lumen between the two impellers. When in use, fluid move through the lumen provided by conduit 1604. The conduits herein are non-permeable, or they can be semi-permeable, or even porous as long as they can still define a lumen. The conduits herein are also flexible, unless it is otherwise indicated. The conduits herein extend completely around (i.e., 360 degrees) at least a portion of the pump portion. In pump portion 1600, conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "O." Conduit 1604 improves impeller pumping dynamics, compared to those that working portion 1600 would have without the conduit.

Expandable member 1602 can have a variety of constructions, and made from a variety of materials. For example, expandable member 1602 may be formed similar to expandable stents or stent-like devices, or any other example provided herein. For example without limitation, expandable member 1602 could have an open-braided construction, such as a 24-end braid, although more or fewer braid wires could be used. Exemplary materials for the expandable member include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive cable 1612 is co-axial with the longitudinal axis in this embodiment. In use, the central region can be placed across a valve, such as an aortic valve. In some embodiments, expandable member 1602 is adapted and constructed to expand to an outermost dimension of 12-24 F (4.0-8.0 mm) where the impellers are axially within the expandable member, and to an outermost dimension of 10-20 F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive cable 1612 rotate within the expandable member and conduit assembly. Drive cable 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein for all purposes.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or U.S. Pat. No. 8,052,749, the disclosures of which are incorporated by reference herein.

Figure 2:
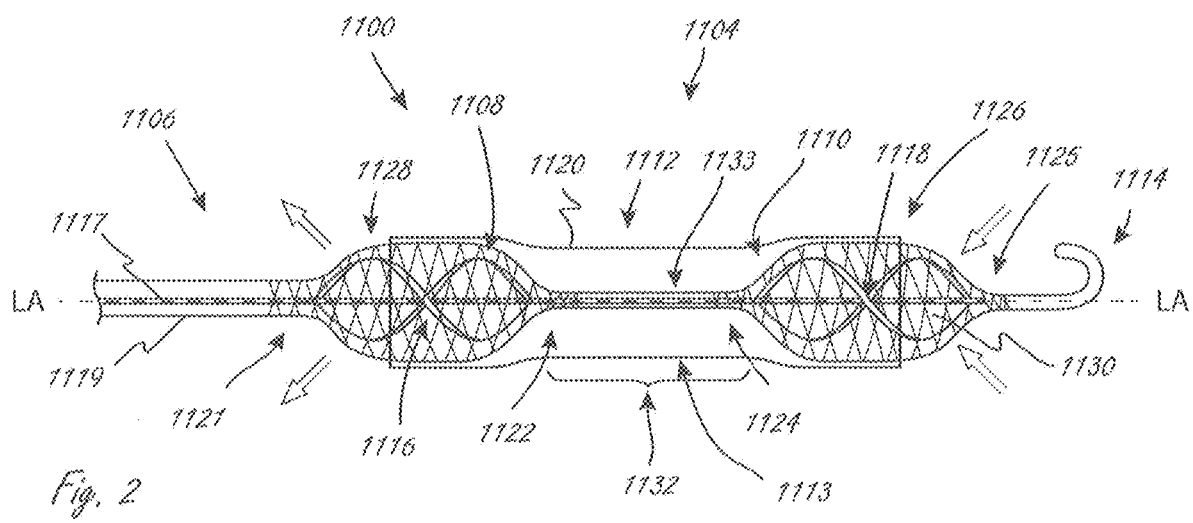
FIG. 2 is a side view of an exemplary working portion that includes a conduit, a plurality of impellers, and a plurality of expandable members.

FIG. 2 is a side view illustrating a deployed configuration (shown extracorporally) of a distal portion of an exemplary embodiment of a fluid movement system. Exemplary system 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable member 1108 and second expandable member 1110, axially spaced apart along a longitudinal axis LA of working portion 1104. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a conduit being coupled to an expandable member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable members help maintain the conduit in an open configuration to create the lumen, while each also creates a working environment for an impeller, described below. Each of the expandable members, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. No. 7,841,976 or 8,052,749, the disclosures of which are incorporated by reference herein for all purposes.

Figure 3A:
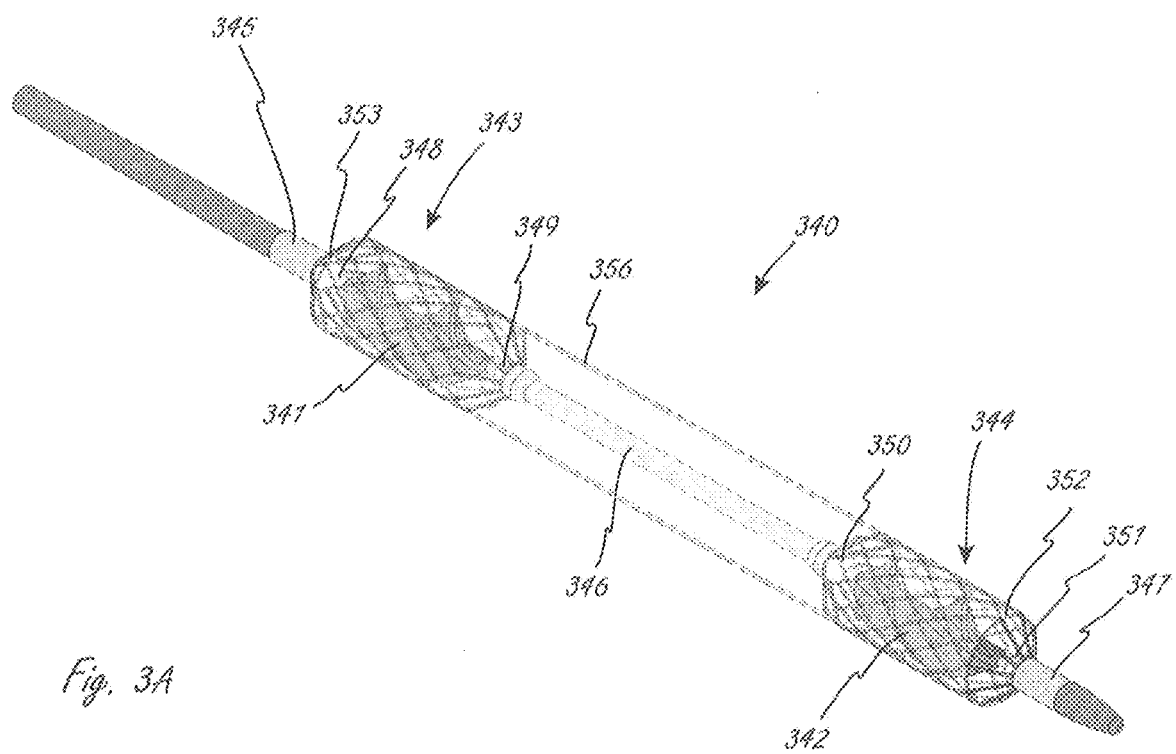
FIGS. 3A, 3B, 3C and 3D illustrate an exemplary working portion that includes a conduit, a plurality of impellers, and a plurality of expandable members.
Figure 3B:
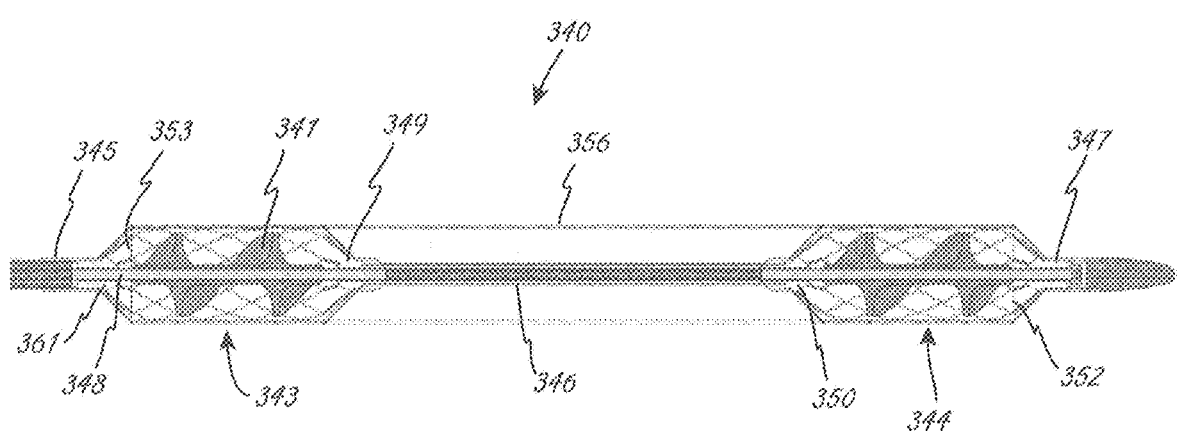
Figure 3C:
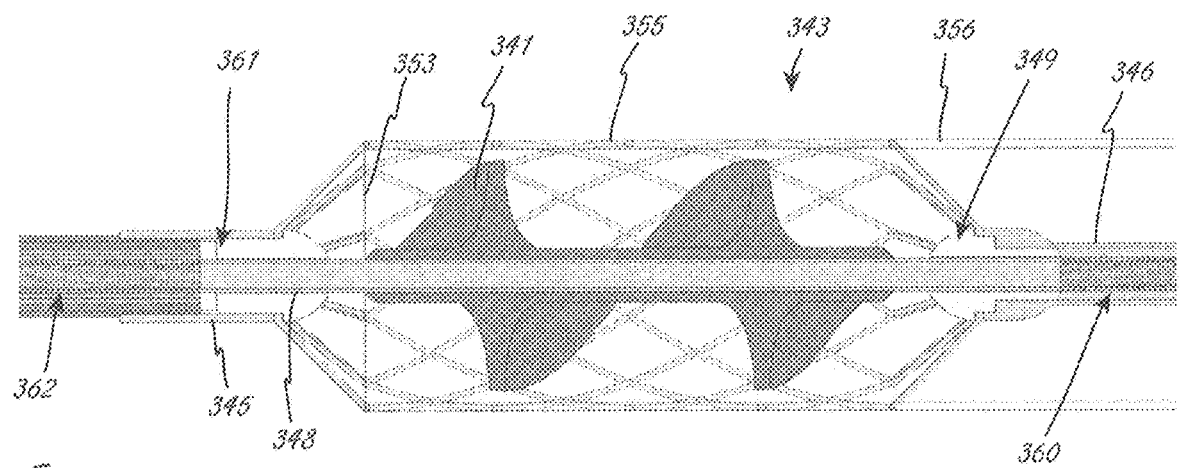
Figure 3D:
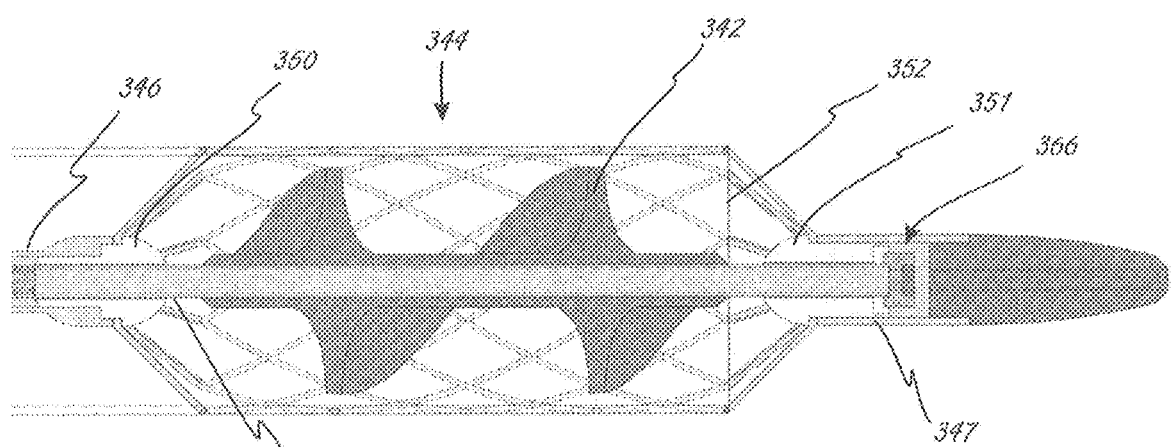

FIGS. 3A-3E show an exemplary working portion that is similar in some ways to the working portion shown in FIG. 2. Working portion 340 is similar to working portion 1104 in that in includes two expandable members axially spaced from one another when the working portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Working portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Working portion 340 includes proximal expandable member 343 and distal expandable member 344, each of which extends radially outside of one of the impellers. The expandable members have distal and proximal ends that also extend axially beyond distal and proximal ends of the impellers, which can be seen in FIGS. 3B-3D. Coupled to the two expandable members is conduit 356, which has a proximal end 353 and a distal end 352. The two expandable members each include a plurality of proximal struts and a plurality of distal struts. The proximal struts in proximal expandable member 343 extend to and are secured to shaft section 345, which is coupled to bearing 361, through which the drive cable extends and is configured and sized to rotate. The distal struts of proximal expandable member 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts of distal expandable member 344 extend to and secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts of distal expandable member extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
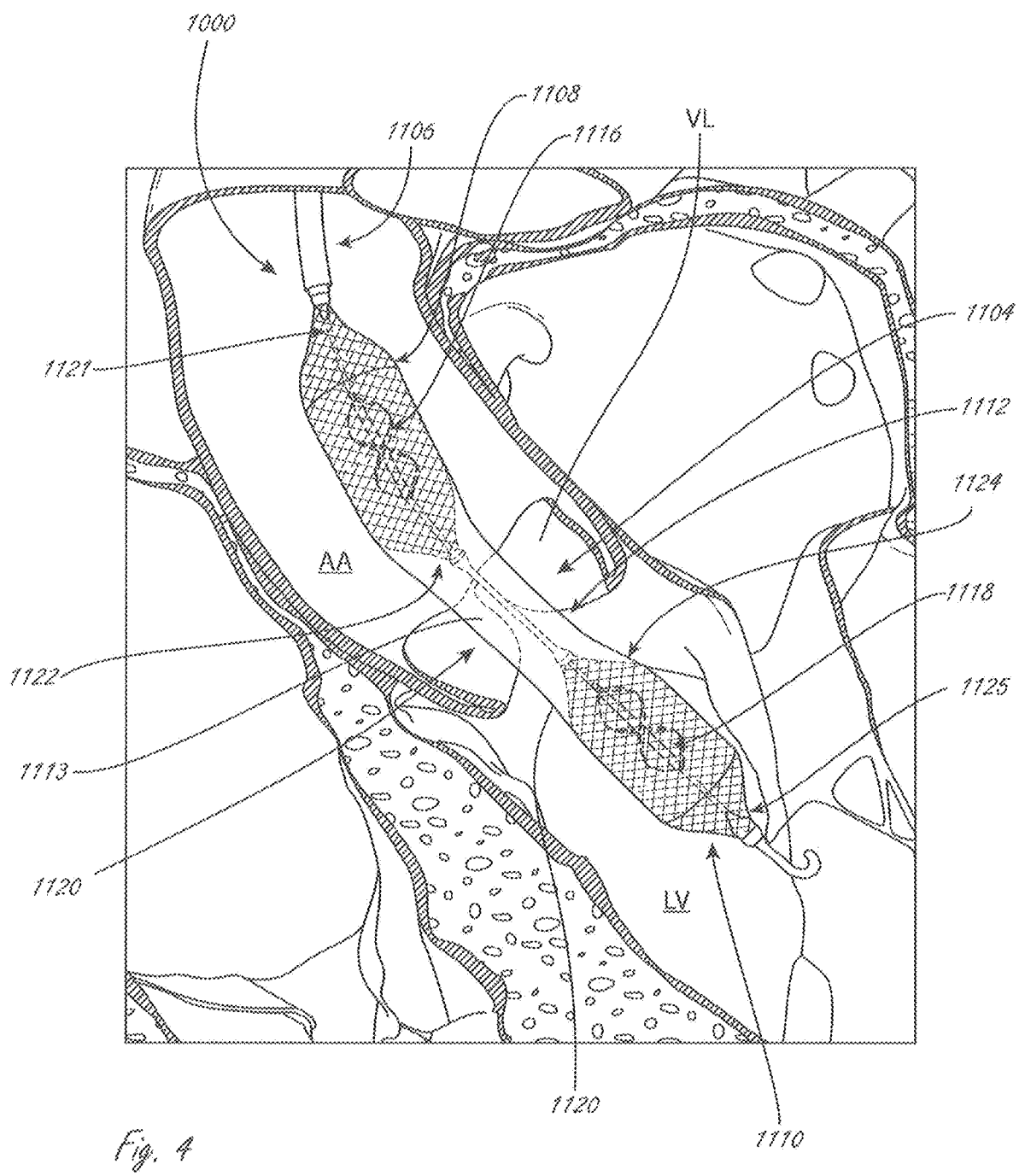
FIG. 4 illustrates an exemplary placement of a working portion, the working portion including a conduit, a plurality of expandable members, and a plurality of impellers.

FIG. 4 illustrates an exemplary placement of working portion 1104 from system 1000 from FIG. 2. One difference shown in FIG. 4 is that the conduit extends at least as far as the ends of the impellers, like in FIGS. 3A-3D. FIG. 4 shows working portion 1104 in a deployed configuration, positioned in place across an aortic valve. Working portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable member 1110, with continued proximal movement allowing first expandable member 1108 to expand.

In this embodiment, second expandable member 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable members 1108 and 1110 causes conduit 1112 to assume a more open configuration, as shown in FIG. 4. Thus, while in this embodiment conduit 1112 does not have the same self-expanding properties as the expandable members, the conduit will assume a deployed, more open configuration when the working end is deployed. At least a portion of central region 1113 of conduit 1112 is positioned at an aortic valve coaptation region. In FIGS. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable member 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of working portion 1104, the position of the working portion can be assessed in any way, such as under fluoroscopy. The position of the working portion can be adjusted at any time during or after deployment. For example, after second expandable member 1110 is released but before first expandable member 1108 is released, working portion 1104 can be moved axially (distally or proximally) to reposition the working portion. Additionally, for example, the working portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9 F sheath and still obtain high enough flow rates when in use, which is not possible with some products currently in development and/or testing. For example, some products are too large to be able to reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable member, referred to 270 generally, and conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit can extend radially within the expandable member so that inner surface of the conduit is radially within the expandable member where it is secured to the expandable member.

Any of the expandable member(s) herein can be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable member is adapted to self-expand when released from within a containing tubular member such as a delivery catheter, a guide catheter, or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figure 6A:
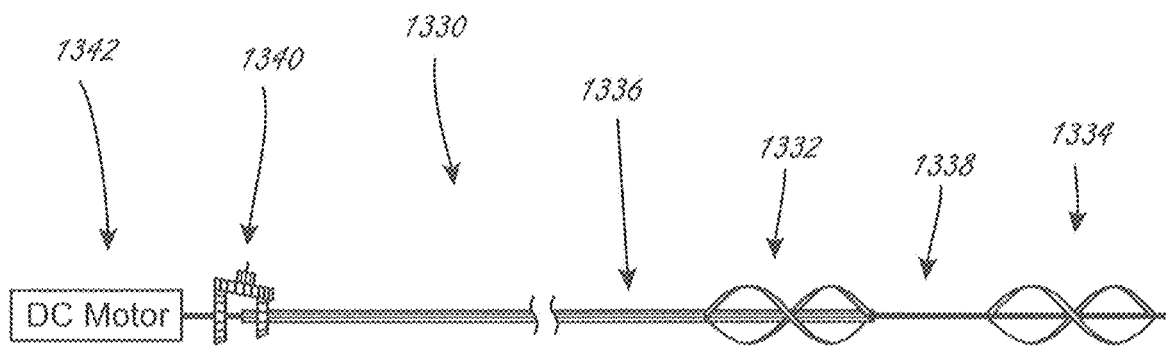
FIG. 6A illustrates at least a portion of an exemplary medical device that has a pump portion, where at least two different impellers can be rotated at different speeds.

In any of the embodiments herein in which the medical device includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

Figure 6B:
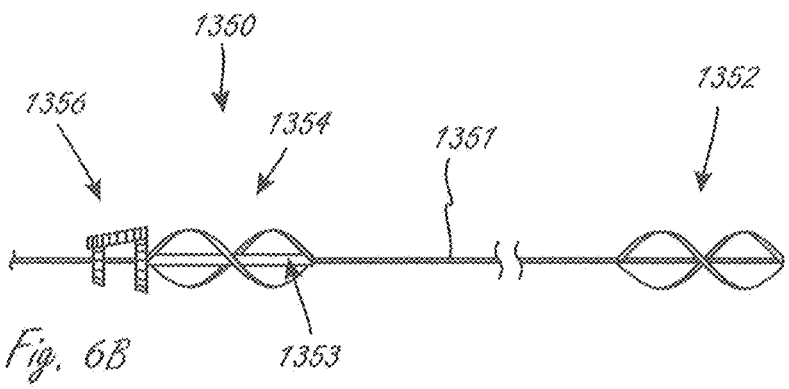
FIG. 6B illustrates at least a portion of an exemplary medical device that has a pump portion, where at least two different impellers can be rotated at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

Figure 7:
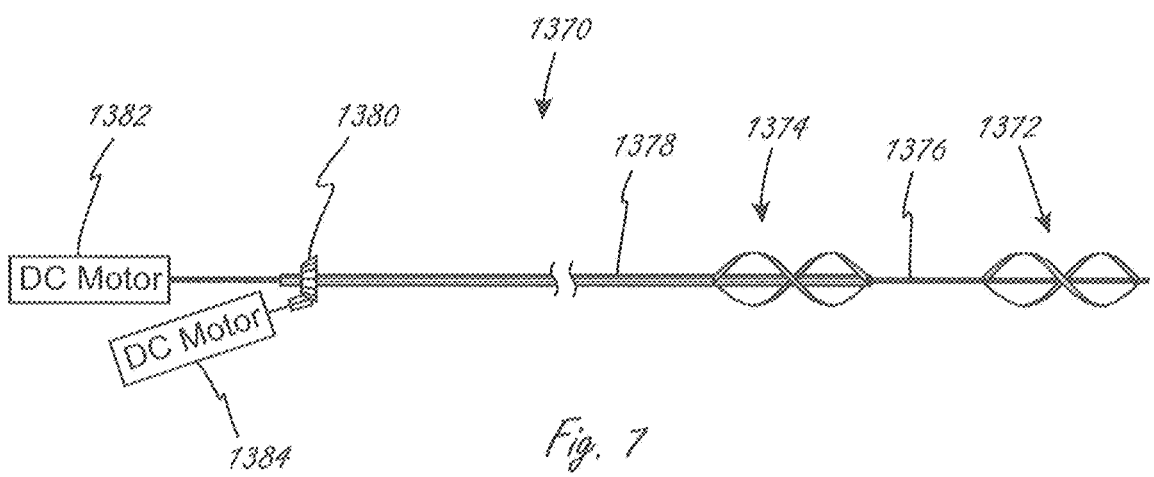
FIG. 7 illustrates at least a portion of an exemplary medical device that has a pump portion.

FIG. 7 shows an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

Figure 6C:
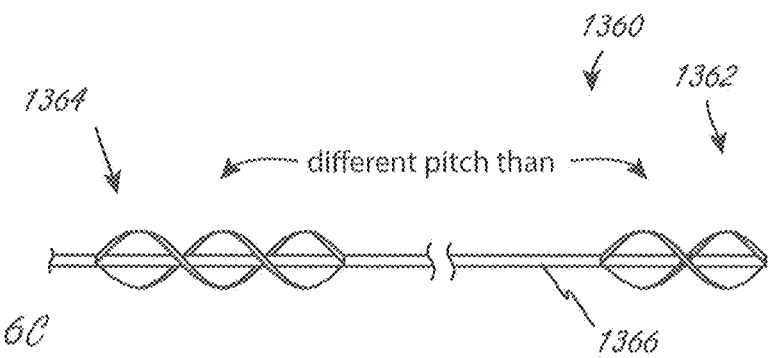
FIG. 6C illustrates at least a portion of an exemplary medical device that has a pump portion with at least two impellers with different pitches.

In some embodiments, a common drive cable or shaft can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion can have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figure 8:
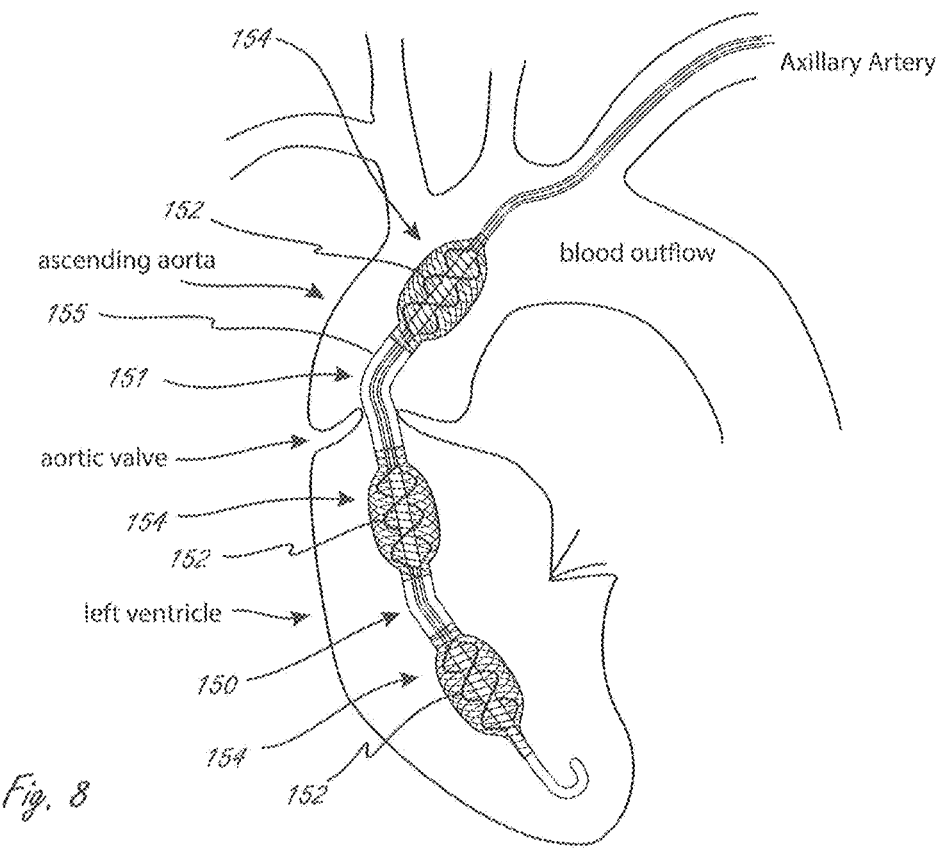
FIG. 8 illustrates a pump portion with multiple impellers, with a bend formed therein between adjacent impellers.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 151 or 152 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. One will appreciate from the description herein, however, that the pump may be introduced and tracked into position in various manner including a femoral approach over the aortic arch.

One aspect of the disclosure is an intravascular blood pump that includes a distal impeller axially spaced from a proximal impeller. In one embodiment, the distal and proximal impellers are separated from each other. For example, the distal and proximal impellers may be connected solely by their individual attachment to a common driveshaft. This is distinct from an impeller having multiple blade rows. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. It can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

Figure 9:
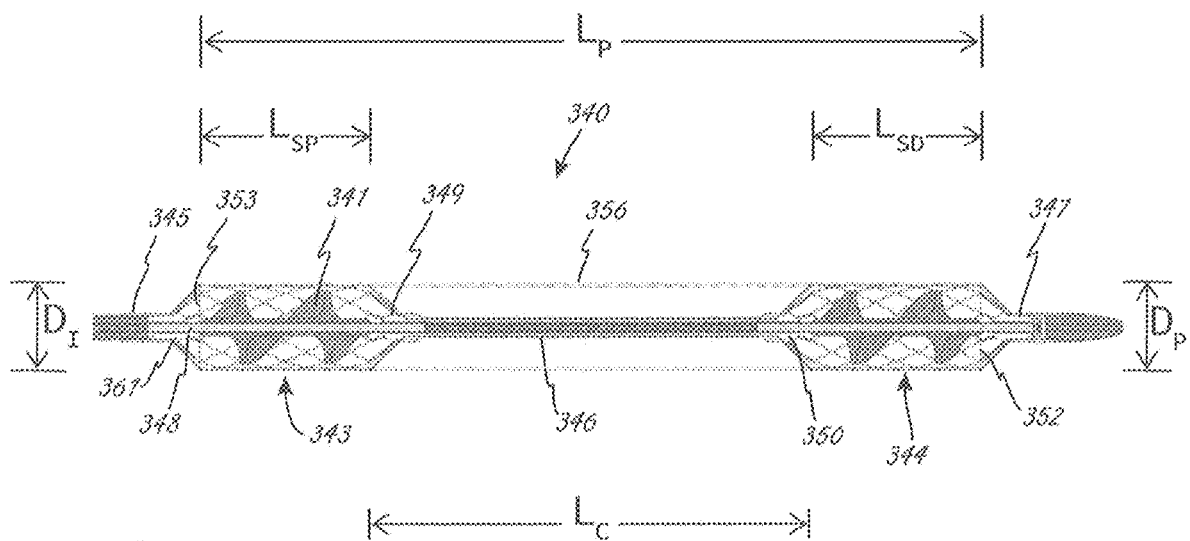
FIG. 9 illustrates a pump portion with a plurality of impellers.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein, at least one of a flow diffuser or diffusers and a stator or stators is/are located between two or more impellers along the catheter shaft. Such a flow diffuser may help to reduce swirl of the fluid and overall increase the efficiency of the multiple impellers as a group.

In any of the embodiments herein, features at the fluid exit of an expandable shroud basket or expandable member are shaped to act as a flow diffuser, such as stent-like struts at the attachments between the catheter shaft outer dimension and the expandable member outer dimension, which can be blade-shaped with a twist directed to change the flow direction of blood. In any of the embodiments herein, one or more portions of the catheter shaft downstream of an impeller may flare to a larger diameter to change the angle of blood flow and cause deceleration of the blood flow to a speed closer to native aortic blood flow. Exemplary locations for a larger diameter downstream of an impeller would be at or near the area where an expandable shroud basket attaches to the catheter shaft, and/or at a bearing housing adjacent the impeller, or on or adjacent an internal motor.

Figure 10:
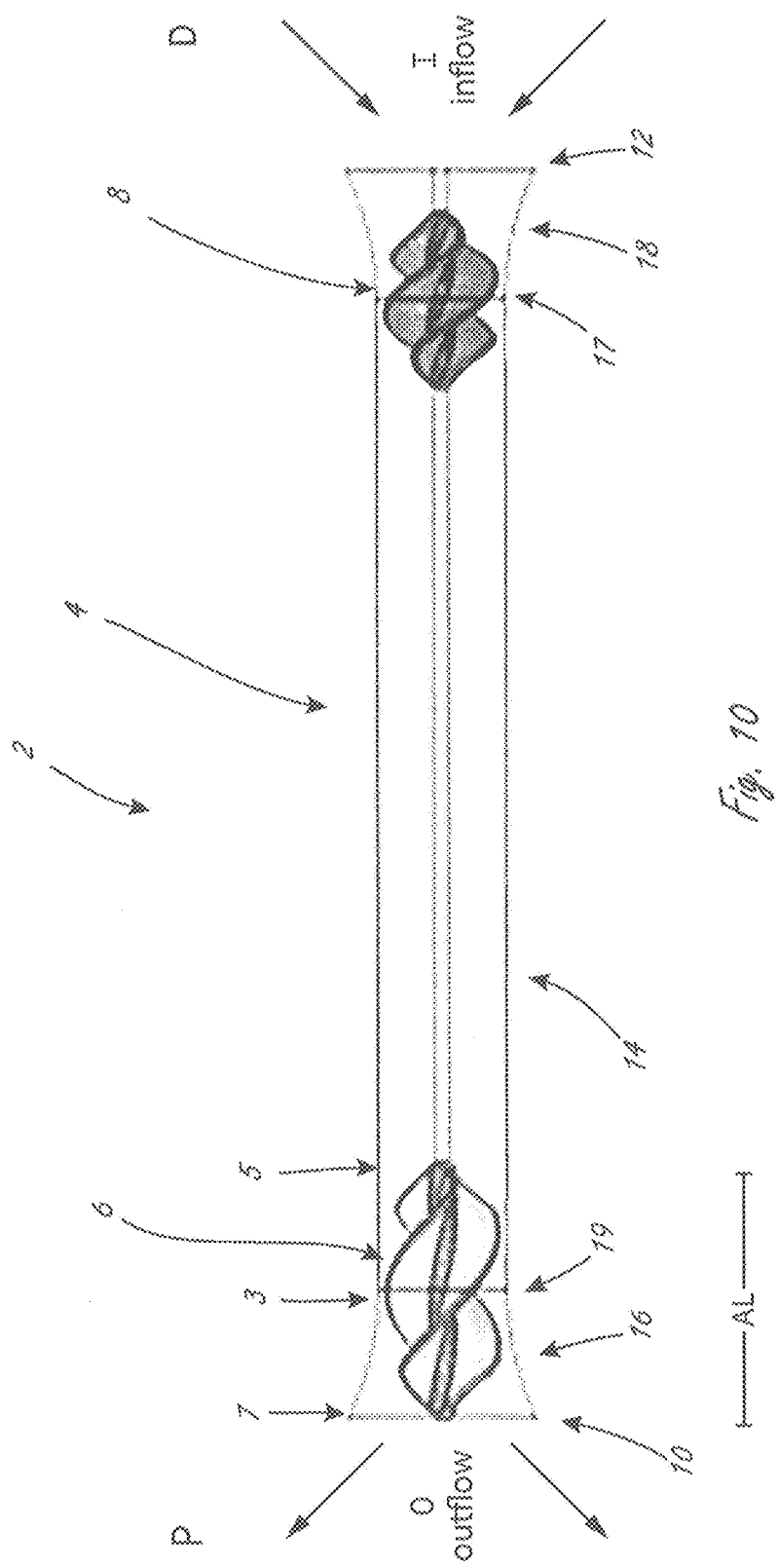
FIG. 10 is a side view of a portion of an exemplary pump portion.

FIG. 10 is a side view of an exemplary embodiment, and will be used as an exemplary embodiment based on experimental findings made by Applicant. FIG. 10 illustrates an exemplary configuration of a fluid lumen in an expanded configuration, as well as exemplary proximal and distal impellers, in expanded configurations. Other aspects of the pump portion are not shown for clarity, but it is understood that other aspects and features may be included in the pump portion as well as the overall system in general (such as other features described herein). FIG. 10 shows a portion of pump portion 2, which includes an expandable housing 4, proximal impeller 6 and distal impeller 8. Expandable housing 4 defines a fluid lumen (aspects of which are described in more detail herein), which in FIG. 10 includes a distal end 12 and proximal end 10. Inflow I and outflow O are illustrated at the distal and proximal ends respectively, which are described in more detail herein. While the general profile of the fluid lumen is shown in FIG. 10, expandable housing 4 may comprise one or more components, such as one or more expandable members (such as those described herein) and/or one or more conduits (such as those described herein). In some embodiments expandable housing 4 includes an expandable structure such as an expandable scaffolding and a deformable material (e.g., a membrane) secured to one another (see, e.g., FIG. 5). In some embodiments an expandable housing is formed from an expandable structure covered with an elastomeric polymer (e.g. polycarbonate urethane or polyurethane). The expandable structure may be a scaffold formed from NiTi, a mesh, and more. The expandable housing defines a fluid lumen therethrough when in the expanded configuration.

The configuration shown in FIG. 10 illustrates the fluid lumen configuration of the expandable housing when the expandable housing is in an expanded configuration. In this example, the fluid lumen includes a substantially constant diameter portion 14, a proximal region 16 with a flared configuration, and a distal region 18 with a flared configuration. In this context, the substantially constant diameter portion can be referred to herein simply as a constant diameter portion, and unless indicated to the contrary, this is meant to imply a substantially constant diameter portion, which is described in more detail herein. The constant diameter portion 14 has a proximal end 19 and a distal end 17. Distal end 17 of the constant diameter region is, in this example, also the proximal end of the distal flared region 18. Proximal end 19 of the constant diameter region is, in this example, also the distal end of the proximal flared region 16.

Part of this disclosure describes unexpected experimental results related to the performance of a pump portion when changing the position of a proximal impeller relative to one more aspects of the fluid lumen. This may be described as, for example, a position of a feature of the proximal impeller (e.g., proximal end, distal end, midpoint, percentage of length, etc.) relative to a position of one more features of the fluid lumen (e.g., proximal end of constant diameter portion, distal end of flared region, proximal end of fluid lumen, etc.).

Results included in this disclosure are based on experiments that altered the axial position of an impeller relative to the fluid lumen of a testing apparatus, while maintaining the configuration of the fluid lumen and the position of a distal impeller. The configuration of the testing apparatus can be used as a basis for the configuration of a portion of the pump portion, an example of which is shown in FIG. 10. FIGS. 11A-11E illustrate exemplary different positions of proximal impeller 6 relative to a fluid lumen of an experimental apparatus, a part of which can be used to mimic an expandable housing that includes a fluid lumen. A central region of the apparatus in FIGS. 11A-11E includes the embodiment in FIG. 10, and all aspects of FIG. 10 and the description thereof apply to FIGS. 11A-11E. The experiments were performed to, for example, characterize and understand how changes in axial position of the impeller can change flow and pressure. Hemolysis was also monitored when changing the axial position.

Figure 11A:
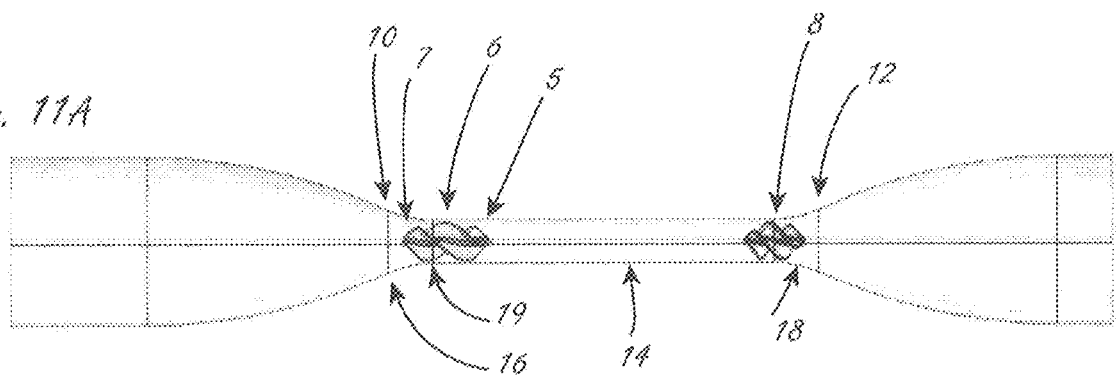
FIGS. 11A, 11B, 11C, 11D, and 11E illustrate exemplary testing, described in more detail herein.
Figure 11B:
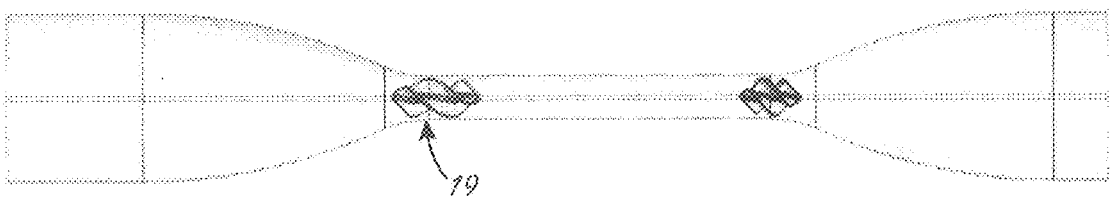
Figure 11C:
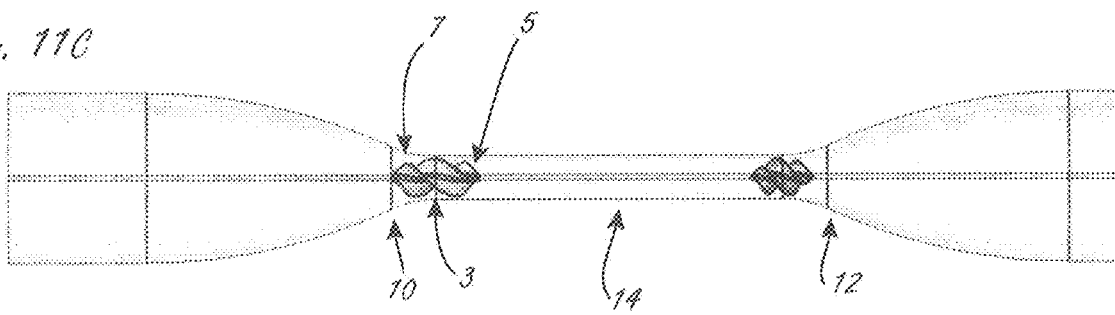
Figure 11D:
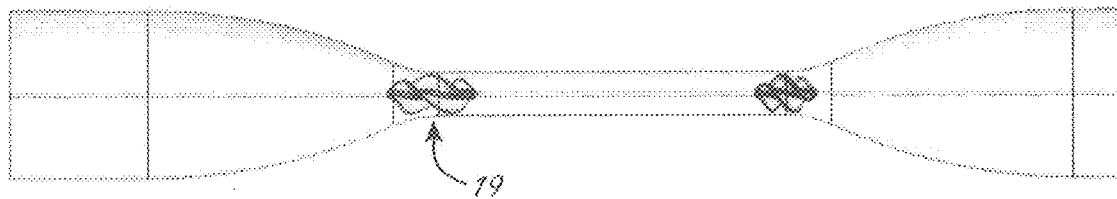
Figure 11E:
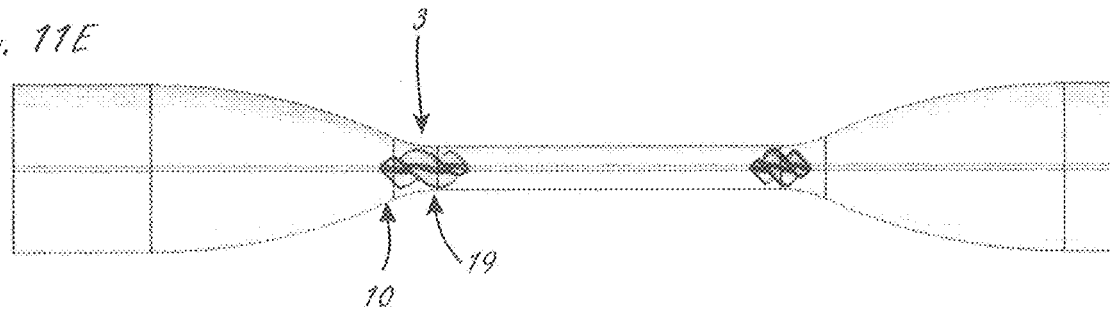

FIG. 11C illustrates what was treated as a baseline axial position for the proximal impeller. FIGS. 11B and 11A illustrate progressive distal movement of the impeller relative to the fluid lumen and relative to the baseline impeller position shown in FIG. 11C. FIGS. 11D and 11E illustrate progressive proximal movement of the impeller relative to the fluid lumen and relative to the baseline impeller position shown in FIG. 11C. The impeller is positioned furthest distally in FIG. 11A and furthest proximally in FIG. 11E.

In this exemplary embodiment and exemplary experiments, the impeller was moved axially in 1 mm increments. For example, the impeller is 1 mm further proximally in FIG. 11D relative to FIG. 11C. In the baseline position shown in FIG. 1C, a midpoint 3 of proximal impeller is axially aligned with a proximal end 19 of the substantially constant diameter portion 14 of the fluid lumen. In this position, a distal half of the impeller is thus disposed in the constant diameter portion 14, and a proximal half of the impeller is disposed in flared region 16.

In some embodiments, the proximal impeller can have an axial length "AL" (measured in the proximal-distal direction; see FIG. 10) of 9 mm, and 4.5 mm of the impeller is disposed in constant diameter portion 14 and 4.5 mm of the impeller is disposed in proximal flared region 16 in the baseline position in FIG. 11C. In FIG. 11A, 6.5 mm of the impeller is disposed in the constant diameter portion 14 and 2.5 mm of the impeller is disposed in flared proximal region 16. In FIG. 11B, 5.5 mm of the impeller is disposed in the constant diameter portion 14 and 3.5 mm of the impeller is disposed in flared proximal region 16. In FIG. 11D, 5.5 mm of the impeller is disposed in the constant diameter portion 14 and 3.5 mm of the impeller is disposed in flared proximal region 16. In FIG. 11E, 2.5 mm of the impeller is disposed in the constant diameter portion 14 and 6.5 mm of the impeller is disposed in flared proximal region 16.

In some embodiments, the proximal impeller can have an axial length "AL" (measured in the proximal-distal direction; see FIG. 10) of 10 mm, and 5 mm of the impeller is disposed in constant diameter portion 14 and 5 mm of the impeller is disposed in proximal flared region 16 in the baseline position in FIG. 11C. In FIG. 11A, 7 mm of the impeller is disposed in the constant diameter portion 14 and 3 mm of the impeller is disposed in flared proximal region 16. In FIG. 11B, 6 mm of the impeller is disposed in the constant diameter portion 14 and 4 mm of the impeller is disposed in flared proximal region 16. In FIG. 11D, 4 mm of the impeller is disposed in the constant diameter portion 14 and 6 mm of the impeller is disposed in flared proximal region 16. In FIG. 11E, 3 mm of the impeller is disposed in the constant diameter portion 14 and 7 mm of the impeller is disposed in flared proximal region 16.

In some embodiments, the proximal impeller can have an axial length "AL" (measured in the proximal-distal direction; see FIG. 10) of 11 mm, and 5.5 mm of the impeller is disposed in constant diameter portion 14 and 5.5 mm of the impeller is disposed in proximal flared region 16 in the baseline position in FIG. 11C. In FIG. 11A, 7.5 mm of the impeller is disposed in the constant diameter portion 14 and 3.5 mm of the impeller is disposed in flared proximal region 16. In FIG. 11B, 6.5 mm of the impeller is disposed in the constant diameter portion 14 and 4.5 mm of the impeller is disposed in flared proximal region 16. In FIG. 11D, 4.5 mm of the impeller is disposed in the constant diameter portion 14 and 6.5 mm of the impeller is disposed in flared proximal region 16. In FIG. 11E, 3.5 mm of the impeller is disposed in the constant diameter portion 14 and 7.5 mm of the impeller is disposed in flared proximal region 16.

In some embodiments, the proximal impeller can have an axial length "AL" (measured in the proximal-distal direction; see FIG. 10) of 12 mm, and 6 mm of the impeller is disposed in constant diameter portion 14 and 6 mm of the impeller is disposed in proximal flared region 16 in the baseline position in FIG. 11C. In FIG. 11A, 8 mm of the impeller is disposed in the constant diameter portion 14 and 4 mm of the impeller is disposed in flared proximal region 16. In FIG. 11B, 7 mm of the impeller is disposed in the constant diameter portion 14 and 5 mm of the impeller is disposed in flared proximal region 16. In FIG. 11D, 5 mm of the impeller is disposed in the constant diameter portion 14 and 7 mm of the impeller is disposed in flared proximal region 16. In FIG. 11E, 4 mm of the impeller is disposed in the constant diameter portion 14 and 8 mm of the impeller is disposed in flared proximal region 16.

In some embodiments, the proximal impeller can have an axial length "AL" (measured in the proximal-distal direction; see FIG. 10) of 13 mm, and 6.5 mm of the impeller is disposed in constant diameter portion 14 and 6.5 mm of the impeller is disposed in proximal flared region 16 in the baseline position in FIG. 11C. In FIG. 11A, 8.5 mm of the impeller is disposed in the constant diameter portion 14 and 4.5 mm of the impeller is disposed in flared proximal region 16. In FIG. 11B, 7.5 mm of the impeller is disposed in the constant diameter portion 14 and 5.5 mm of the impeller is disposed in flared proximal region 16. In FIG. 11D, 5.5 mm of the impeller is disposed in the constant diameter portion 14 and 7.5 mm of the impeller is disposed in flared proximal region 16. In FIG. 11E, 4.5 mm of the impeller is disposed in the constant diameter portion 14 and 8.5 mm of the impeller is disposed in flared proximal region 16.

In some embodiments, the proximal impeller can have an axial length "AL" (measured in the proximal-distal direction; see FIG. 10) of 14 mm, and 7 mm of the impeller is disposed in constant diameter portion 14 and 7 mm of the impeller is disposed in proximal flared region 16 in the baseline position in FIG. 11C. In FIG. 11A, 9 mm of the impeller is disposed in the constant diameter portion 14 and 5 mm of the impeller is disposed in flared proximal region 16. In FIG. 11B, 8 mm of the impeller is disposed in the constant diameter portion 14 and 6 mm of the impeller is disposed in flared proximal region 16. In FIG. 11D, 6 mm of the impeller is disposed in the constant diameter portion 14 and 8 mm of the impeller is disposed in flared proximal region 16. In FIG. 11E, 5 mm of the impeller is disposed in the constant diameter portion 14 and 9 mm of the impeller is disposed in flared proximal region 16.

In some embodiments, the proximal impeller can have an axial length "AL" (measured in the proximal-distal direction; see FIG. 10) of 15 mm, and 7.5 mm of the impeller is disposed in constant diameter portion 14 and 7.5 mm of the impeller is disposed in proximal flared region 16 in the baseline position in FIG. 11C. In FIG. 11A, 9.5 mm of the impeller is disposed in the constant diameter portion 14 and 5.5 mm of the impeller is disposed in flared proximal region 16. In FIG. 11B, 8.5 mm of the impeller is disposed in the constant diameter portion 14 and 6.5 mm of the impeller is disposed in flared proximal region 16. In FIG. 11D, 6.5 mm of the impeller is disposed in the constant diameter portion 14 and 8.5 mm of the impeller is disposed in flared proximal region 16. In FIG. 11E, 5.5 mm of the impeller is disposed in the constant diameter portion 14 and 9.5 mm of the impeller is disposed in flared proximal region 16.

In some embodiments, the proximal impeller can have an axial length "AL" (measured in the proximal-distal direction; see FIG. 10) of 16 mm, and 8 mm of the impeller is disposed in constant diameter portion 14 and 8 mm of the impeller is disposed in proximal flared region 16 in the baseline position in FIG. 11C. In FIG. 11A, 10 mm of the impeller is disposed in the constant diameter portion 14 and 6 mm of the impeller is disposed in flared proximal region 16. In FIG. 11B, 9 mm of the impeller is disposed in the constant diameter portion 14 and 7 mm of the impeller is disposed in flared proximal region 16. In FIG. 11D, 7 mm of the impeller is disposed in the constant diameter portion 14 and 9 mm of the impeller is disposed in flared proximal region 16. In FIG. 11E, 6 mm of the impeller is disposed in the constant diameter portion 14 and 10 mm of the impeller is disposed in flared proximal region 16.

In some embodiments, the proximal impeller can have an axial length "AL" (measured in the proximal-distal direction; see FIG. 10) of 17 mm, and 8.5 mm of the impeller is disposed in constant diameter portion 14 and 8.5 mm of the impeller is disposed in proximal flared region 16 in the baseline position in FIG. 11C. In FIG. 11A, 10.5 mm of the impeller is disposed in the constant diameter portion 14 and 6.5 mm of the impeller is disposed in flared proximal region 16. In FIG. 11B, 9.5 mm of the impeller is disposed in the constant diameter portion 14 and 7.5 mm of the impeller is disposed in flared proximal region 16. In FIG. 11D, 7.5 mm of the impeller is disposed in the constant diameter portion 14 and 9.5 mm of the impeller is disposed in flared proximal region 16. In FIG. 11E, 6.5 mm of the impeller is disposed in the constant diameter portion 14 and 10.5 mm of the impeller is disposed in flared proximal region 16.

The relative positions of the proximal impeller portions can also be described as percentages of impeller length rather than length dimensions. In FIG. 11A, 35% of the length of the proximal impeller is disposed proximal to the constant diameter portion 14 and 65% of the length of the impeller is disposed in the constant diameter portion 14. In FIG. 11B, 42% of the length of the proximal impeller is disposed proximal to the constant diameter portion 14 and 58% of the length of the impeller is disposed in the constant diameter portion 14. In FIG. 11C, 50% of the length of the proximal impeller is disposed proximal to the constant diameter portion 14 and 50% of the length of the impeller is disposed in the constant diameter portion 14. In FIG. 11D, 58% of the length of the proximal impeller is disposed proximal to the constant diameter portion 14 and 42% of the length of the impeller is disposed in the constant diameter portion 14. In FIG. 11E, 65% of the length of the proximal impeller is disposed proximal to the constant diameter portion 14 and 35% of the length of the impeller is disposed in the constant diameter portion 14.

In the experiment, the pump portion of the testing apparatus was operated at a constant rotation rate of 30,500 RPM, and flow rates were measured for the different axial positions of the proximal impeller based a constant rotation rate.

Estimated flow rates are provided herein, that were extrapolated to 60 mm Hg relative to the baseline position shown in FIG. 11C. The flow rate of the pump portion when the impeller was in the position in FIG. 11D was about 5% more than the flow rate of the baseline position in FIG. 11C (e.g., 4.9% more). The flow rate of the pump portion when the impeller was in the position in FIG. 11E was about 11% more than the flow rate of the baseline position in FIG. 11C (e.g., 10.7% more). The flow rate of the pump portion when the impeller was in the position in FIG. 11B was about 18% less than the flow rate of the baseline position in FIG. 11C (e.g., 18.2% less). The flow rate of the pump portion when the impeller was in the position in FIG. 11A was about 41% less than the flow rate of the baseline position in FIG. 11C (e.g., 41.2% less). This information is also presented in the table below.

TABLE 1

| | Midpoint of impeller relative to proximal end of constant diameter portion (mm) | % of the proximal impeller axial length that is proximal to constant diameter portion | Impact on flow (relative to FIG. C) |
| --- | --- | --- | --- |
| FIG. 11A | −2 mm | 35% | 41% decrease |
| FIG. 11B | −1 mm | 42% | 18% decrease |
| FIG. 11C | 0 | 50% | Baseline |
| FIG. 11D | 1 mm | 58% | 5% increase |
| FIG. 11E | 2 mm | 65% | 11% increase |

The magnitude of the differences in the measured flows rate due to relatively small changes in axial positioning were unexpected and surprising. These unexpected results indicated that relatively small changes in axial position can dramatically change the flow rate. The experimental results also indicated that for pump portion designs in which a distal region of a proximal impeller is positioned in a substantially constant diameter region of a fluid lumen and a proximal region is disposed proximal to the substantially constant diameter region, there are positions or locations where the impeller can be placed that will result in more favorable flow rates relative to other positions. Alternatively stated, there are positions or locations where the impeller can be positioned, relative to the constant diameter portion, that may result in suboptimal flow rates, and even flow rates that could prevent the pump portion from achieving desired operating parameters.

One aspect of the disclosure is an intravascular blood pump that includes an impeller, optionally a proximal impeller, wherein a portion of the proximal impeller is disposed in a substantially constant diameter portion of a fluid lumen and a portion is disposed outside of the substantially constant diameter portion. The embodiment in FIG. 10 is an example of this aspect. As shown by the experimental results herein, there can be significant changes in flow by moving a proximal impeller relative to the fluid lumen, such as by changing the length of the impeller that extends proximally beyond a proximal end of a substantially constant diameter region of a fluid lumen. The data presented herein illustrates observed changes in pump portion performance based on exemplary tests and modeling. While some exemplary relative positions herein illustrate some noticed improvements in pump performance, it is contemplated that additional relative positions not specifically tested herein may provide benefits to pump performance, even if not specifically tested herein, and even if the improvements are not as dramatic as some other improvements herein. The disclosure and ranges below may thus provide pump portion performance that is improved relative to other impeller positions, and are considered part of the disclosure herein. Even if claims presented herein include one or more aspects of the disclosure more closely related to the experimental results, it is intended that the disclosure include other quantitative or qualitative aspects that may not be specifically described in the experimental results. For example, for some impellers designs, flow may be optimized or desired if 20% to 40% of a proximal impeller extends proximally beyond a proximal end of a constant diameter portion.

In some embodiments, at least 20% and up to 90% of the impeller (axial length) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, optionally up to 35% of the impeller, optionally up to 30% of the impeller, optionally up to 25% of the impeller, is disposed proximal to a proximal end of the constant diameter portion.

In some embodiments, at least 25% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 30% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 35% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 40% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller is disposed proximal to a proximal end of the constant diameter portion.

In some embodiments, at least 45% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller is disposed proximal to a proximal end of the constant diameter portion.

In some embodiments, at least 50% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller is disposed proximal to a proximal end of the constant diameter portion.

In some embodiments, at least 55% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller is disposed proximal to a proximal end of the constant diameter portion.

In some embodiments, at least 60% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller is disposed proximal to a proximal end of the constant diameter portion.

In some embodiments, at least 65% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller is disposed proximal to a proximal end of the constant diameter portion.

In some embodiments, at least 70% and up to 90% of the impeller (measured axially) is disposed proximal to a proximal end of the constant diameter portion, optionally up to 85% of the impeller, optionally up to 80% of the impeller, optionally up to 75% of the impeller, is disposed proximal to a proximal end of the constant diameter portion.

In some embodiments, at least 75% and up to 90% of the impeller (measured axially) is disposed proximal to a proximal end of the constant diameter portion, optionally up to 85% of the impeller, optionally up to 80% of the impeller is disposed proximal to a proximal end of the constant diameter portion.

In some embodiments, at least 80% and up to 90% of the impeller (measured axially) is disposed proximal to a proximal end of the constant diameter portion, optionally up to 85% of the impeller is disposed proximal to a proximal end of the constant diameter portion.

While FIG. 10 illustrates a portion of an exemplary portion that is taken from the testing apparatus in FIG. 11C, it is understood that the disclosure also includes pump portions that are generally shown in FIG. 10, but include proximal impellers that are have relative positions shown in FIGS. 11D and 11E. This disclosure thus implicitly and inherently includes pump portions that include all of the features of FIG. 10, but are as modified as shown in FIGS. 11A, 11B, 11D, and 11E, even though those figures are not expressly provided herein.

Some pump portions herein may have a proximal impeller that extends proximally beyond a proximal end of a fluid lumen. For example, the proximal impellers shown in FIGS. 11D and 11E, when incorporated into a pump portion such as that shown in FIG. 10, extend proximally beyond a proximal end of a fluid lumen.

Some of the fluid lumens herein have one or more end regions that have one or more surface that behave as a fluid diffuser. For example, flared proximal region 16 in FIG. 10 is an example of a proximal end region that has one or more surfaces that function as a fluid diffuser for turbulent flow. Any of the disclosure herein related to axial impeller position relative to a fluid lumen can apply to fluid lumens herein that have one or more end regions that have one or more surfaces that behave as a fluid diffuser.

Some of the fluid lumens herein have one or more end regions that have a flared configuration. For example, proximal region 16 in FIG. 10 is an example of a proximal fluid lumen region that has a flared configuration. Any of the disclosure herein related to axial impeller position relative to a fluid lumen can apply to fluid lumens herein that have a proximal region with a flared configuration. As used herein, a flared configuration refers generally to configurations that progressively extend further radially outward. A flared configuration might, but does not necessarily require, a configuration that continuously extends further radially outward along the entire axial length of the flared region. FIG. 10 is an example of a continuous flared configuration. Other configurations are possible in which only a portion of the proximal region has a continuous flare while other portions of the proximal region do not include a continuous flare. For example, a proximal region could include a step wise configuration with one or more continuous flared regions.

In some embodiments the flared configuration can be described in terms of a change in radial dimension (compared to the radial dimension of a substantially constant diameter region) per change in axial length. In any of the embodiments herein the flared configuration can have a mean (or average) change in radius per change in axial length that is from 5-100%, such as 10-75%, such as 15-50%, or such as 20-30%.

In any of the embodiments herein, the outlet may have an asymmetrical shape, e.g., a torus shape to promote centrifugal flow. The flared outlet does not need to have a smooth surface. For example, the outlet walls may have edges or sharp curves. The outlet walls may be non-planar (e.g., dimpled surfaces).

One aspect of the exemplary embodiment shown in FIG. 10 (including any pump portions that are modified versions of FIG. 10 and include relative impeller positions shown in FIGS. 11A, 11B, 11D, and 11E) is that the impeller and fluid lumen configurations shown (including the proximal end configuration of the fluid lumen) described provide for change in flow rates as the position of the impeller is changed. One exemplary aspect of incorporating the impeller and fluid lumen configurations shown in FIGS. 10 and 11A-11E is that when the proximal impeller is moved at least 2 mm proximally relative to an initial position, and moved so that less of the proximal impeller is (but not all of it) disposed in a substantially constant diameter portion of the fluid lumen, the flow rate of the pump portion, at 60 mm Hg, increases at least 10%. The initial position may be a position where the midpoint of the impeller is axially aligned with a proximal end of the substantially constant diameter portion.

Another exemplary aspect of incorporating the impeller and fluid lumen configurations shown in FIGS. 10 and 11A-11E is that when the proximal impeller is moved at least 2 mm distally relative to an initial position, and moved so that more of the proximal impeller is (but not all of it) disposed in a substantially constant diameter portion of the fluid lumen, the flow rate of the pump portion, at 60 mm Hg, decreases at least 40%. Again, the initial position may be a position where the midpoint of the impeller is axially aligned with a proximal end of the substantially constant diameter portion.

One aspect of this disclosure is an intravascular blood pump with a collapsible housing comprising a fluid lumen, the fluid lumen having a distal end and a proximal end. The blood pump also includes a collapsible distal impeller axially spaced from a collapsible proximal impeller, the distal impeller having an expanded configuration and the proximal impeller having an expanded configuration. At least a portion of the distal and proximal impellers is disposed between the distal and proximal ends of the fluid lumen. The embodiments in FIGS. 10 and 11A-11E are examples of this aspect. In the exemplary embodiments of FIGS. 11D and 11E, the proximal impeller is configured to generate more 50% of the pressure generated by the blood pump, and the distal impeller is configured to generate less than 50% of the pressure generated by the blood pump. This can alternatively be stated as the proximal impeller is configured to do more than 50% of the work of the blood pump, with the distal impeller configured to do less than 50% of the work of the blood pump. In this context, work is a function of pressure and volume. Since the flow rate (volume of fluid per unit time) through the pump is generally the same for both impellers, each impeller can be configured to have a different contribution to the pressure generated by the pump, which can be different by design.

In the embodiment in FIG. 10, the blood pump does not include a vane assembly, stator blade, or any other flow modifying structures axially between the proximal and distal impellers.

In some embodiments, the proximal impeller generates more than 55% of the pressure generated by the blood pump, and the distal impeller generates less than 45% of the pressure generated by the blood pump. In some embodiments, the proximal impeller generates more than 60% of the pressure of the blood pump, and the distal impeller generates less than 40% of the pressure of the blood pump. In some embodiments, the proximal impeller generates more than 70% of the pressure of the blood pump, and the distal impeller generates less than 30% of the pressure of the blood pump. In some embodiments, the proximal impeller generates about 80% of the pressure of the blood pump, and the distal impeller generates about 20% of the pressure of the blood pump.

For any of the disclosure herein referring to the distal and proximal impellers generating a certain percentage of the pressure generated the pump, pressure measurements can be taken at a location distal to the distal impeller, at a location axially in between the impellers, and a location proximal to the proximal impeller, so that pressure differentials for each impeller can be calculated.

One aspect of this disclosure is a method of intravascularly pumping blood in a subject. The method can include positioning a pump housing fluid lumen first end in a first anatomical region (such as a left ventricle), positioning a distal impeller of the blood pump in the first anatomical region (such as a left ventricle), positioning a proximal impeller of the blood pump in a second anatomical location (such as an ascending aorta), positioning a pump housing fluid lumen second end in the second anatomical location (such as an ascending aorta), positioning at least a portion of a central region of the fluid lumen across an anatomical location (such as an aortic valve), and creating a flow path between the fluid lumen first end positioned in the first anatomical location (e.g., left ventricle) and the fluid lumen second end positioned in the second anatomical location (e.g., ascending aorta) such that the distal impeller and the proximal impeller can pump blood through the fluid lumen. The method can include rotating the distal impeller and proximal impeller, thereby pumping blood, which results in the proximal impeller generating more than 50% of the pressure generated by the blood pump and the distal impeller generating less than 50% of the pressure generated by the blood pump. The method can include the distal and proximal impellers generating any amount of pressure as is described herein. Any other suitable method step can be included in this method aspect unless specifically indicated to the contrary. The method can alternatively be stated as, instead of the individual impellers generating more or less than a particular percentage of pressure generated by the pump, the individual impellers can be performing more than or less than a percentage of work of the blood pump.

It has been found that distributing loads over two impellers (as is described herein), compared to single impeller designs, can lead to higher pump efficiency, lower pump speeds, and thus a decrease in hemolysis.

In FIGS. 10A and 11A-E, the proximal region of the impeller that is disposed outside of the substantially constant diameter region of the fluid lumen may be referred to as a proximal impeller region that is disposed proximal to a proximal end of the substantially constant diameter region, regardless of the specific configuration of the fluid lumen proximal to the constant diameter region. In FIGS. 10 and 11A-11E, a portion of the proximal impeller is disposed in the substantially constant diameter portion.

The test apparatus shown in FIGS. 11A-11E includes proximal and distal region that are not included in the exemplary fluid lumen in the embodiment in FIG. 10. While those enlarged portions are not included in the exemplary fluid lumen in FIG. 10, those regions may in some circumstances approximate one or more anatomical regions in which the pump portion is positioned. The term approximate in this context refers to having some characteristics of an anatomical location even if the actual anatomical features are different in one or more, and perhaps many, regards. For example, the enlarged proximal region in FIGS. 11A-E may in some ways be similar to one or more aspects of an ascending aorta, even if an ascending aorta is different in some regards.

The disclosure herein includes some embodiments of a pump portion that are described as having a fluid lumen with a substantially constant diameter portion. For example, the embodiment in FIG. 10 includes a substantially constant diameter portion 14. The phrase substantially constant can include some degree of variation in diameter. For example, some expandable housings herein include a reinforcing structure (which may be referred to as an expandable member) and a conduit such a membrane secured to the reinforcing structure. The manner in which these two components may be secured or assembled together can cause some minor variation in diameter. For example, if a membrane is applied to inner and/or outer surfaces of a reinforcing member (e.g., one or more stent-like devices), there may be slight variations in diameter between the locations where the membrane is positioned on an external or internal surface of the reinforcing and locations directly adjacent to those secured locations where a reinforcing member is not present. Those differences may be of small order (e.g. millimeters or microns), but even if they are larger, the intent is that those types of variations fall within the umbrella phrase of substantially constant. An alternative way of interpreting the phrase substantially constant is that the design of the fluid lumen in that region is intended to have as near as possible a constant diameter, even if particular designs or manufacturing constraints cause it to have some variation. A further alternative way of interpreting substantially constant is to inquire if the region of the fluid lumen is intended, from a design and functionality perspective, to have a variable diameter in that region. If the intent is to have a variable diameter and for the variable diameter to impart particular functionality, it may fall outside the scope of a substantially constant diameter portion. One of skill will appreciate from the description herein that the substantially constant diameter portion does not need to be formed as a tube and may take a variety of forms and shapes. As used herein, substantially constant diameter portion may refer to the main section of the fluid lumen. In certain embodiments, this section has a substantially constant diameter to reduce flow disturbances along the inner walls of the lumen and/or reduce the risk of trauma to the outer anatomy (e.g., the aortic valve leaflets). However, this section may take other forms depending on the application. For example, this portion may have dimples, curves, and the like to modify the flow therethrough as desired. In certain embodiments, substantially constant diameter portion may merely refer to the main portion of the fluid lumen as differentiated from the inlet and outlet portions.

Any of the other disclosure herein may be incorporated into the FIG. 10 embodiment unless specifically indicated to the contrary. For example, any of the suitable expandable structures can be incorporated into the embodiment in FIG. 10.

What is claimed is:

1. An intravascular blood pump, comprising:
   an elongate shaft;
   a collapsible housing extending distally from the elongate shaft and including an expandable blood conduit that defines a blood lumen between a proximal end and a distal end, the collapsible housing further including a proximal portion, a central portion, and a distal portion, the proximal portion extending proximally beyond the proximal end of the fluid conduit, the distal portion extending distally beyond the distal end of the fluid conduit, the central portion being more flexible than the proximal portion and the distal portion; and
   a collapsible impeller having an expanded configuration, a portion of the collapsible impeller being disposed outside of the fluid conduit while a remaining portion of the collapsible impeller is disposed in the fluid conduit.

2. The blood pump of claim 1, wherein the collapsible impeller is disposed in the proximal portion of the expandable housing, wherein the portion of the collapsible impeller disposed outside of the fluid conduit is proximal to the fluid conduit.

3. The blood pump of claim 1, wherein from 20% to 50% of the impeller, measured along an axial length of the impeller, is disposed outside of the fluid conduit.

4. The blood pump of claim 1, wherein from 20% to 45% of the impeller, measured along an axial length of the impeller, is disposed outside of the fluid conduit.

5. The blood pump of claim 1, wherein from 20% to 40% of the impeller, measured along an axial length of the impeller, is disposed outside of the fluid conduit.

6. The blood pump of claim 1, wherein about 20% of the impeller, measured along an axial length of the impeller, is disposed outside of the fluid conduit.

7. The blood pump of claim 1, wherein about 25% of the impeller, measured along an axial length of the impeller, is disposed outside of the fluid conduit.

8. The blood pump of claim 1, wherein about 30% of the impeller, measured along an axial length of the impeller, is disposed outside of the fluid conduit.

9. The blood pump of claim 1, wherein about 35% of the impeller, measured along an axial length of the impeller, is disposed outside of the fluid conduit.

10. The blood pump of claim 1, wherein about 40% of the impeller, measured along an axial length of the impeller, is disposed outside of the fluid conduit.

11. The blood pump of claim 1, wherein the impeller has a tapered proximal end region.

12. The blood pump of claim 11, wherein the tapered proximal end region is disposed at least partially within a flared proximal end of the fluid conduit.

13. The blood pump of claim 1, wherein the fluid conduit has a flared proximal end region.

14. The blood pump of claim 1, wherein the fluid conduit has a flared distal end region.

15. The blood pump of claim 1, wherein the impeller is disposed entirely within the expandable member.

16. The blood pump of claim 15, wherein the proximal portion of the expandable member tapers inward proximal to a proximal end of the impeller.

17. The blood pump of claim 1, wherein the expandable member has a distal portion extending distally beyond the distal end of the fluid conduit.

18. The blood pump of claim 1, wherein at least a portion of the collapsible housing has a helical configuration.

19. The blood pump of claim 18, wherein the proximal portion and the distal portion of the collapsible housing have a mostly axial configuration.

20. The blood pump of claim 1, wherein the proximal portion and the distal portion of the collapsible housing have a mostly axial configuration.

* * * * *